(12) United States Patent
Kermani et al.

(10) Patent No.: US 6,872,299 B2
(45) Date of Patent: Mar. 29, 2005

(54) PASSIVE SAMPLE DETECTION TO INITIATE TIMING OF AN ASSAY

(75) Inventors: Mahyar Z. Kermani, Pleasanton, CA (US); Timothy Ohara, San Ramon, CA (US); Maria Teodorczyk, San Jose, CA (US)

(73) Assignee: LifeScan, Inc., Milpitas, CA (US)

( * ) Notice: Subject to any disclaimer, the term of this patent is extended or adjusted under 35 U.S.C. 154(b) by 473 days.

(21) Appl. No.: 10/013,856

(22) Filed: Dec. 10, 2001

(65) Prior Publication Data

US 2003/0106809 A1 Jun. 12, 2003

(51) Int. Cl.[7] ............................................. G01N 27/327
(52) U.S. Cl. .................... 205/777.5; 205/775; 204/400; 204/403.14
(58) Field of Search ........................ 204/403.01–403.14; 205/775, 777.5, 779, 787, 792, 789, 778

(56) References Cited

U.S. PATENT DOCUMENTS

| | | | |
|---|---|---|---|
| 4,935,105 A | * | 6/1990 | Churchouse ................. 205/778 |
| 5,266,179 A | | 11/1993 | Nankai et al. ............... 204/401 |
| 5,366,609 A | | 11/1994 | White et al. ............ 204/403.04 |
| 5,413,690 A | | 5/1995 | Kost et al. ................ 205/777.5 |
| 5,508,171 A | | 4/1996 | Walling et al. |
| 5,796,345 A | * | 8/1998 | Leventis et al. ............. 340/604 |
| 5,909,114 A | * | 6/1999 | Uchiyama et al. ............ 324/94 |
| 6,193,873 B1 | | 2/2001 | Ohara et al. ................. 205/792 |
| 6,531,040 B2 | * | 3/2003 | Musho et al. ................ 204/401 |

FOREIGN PATENT DOCUMENTS

| | | | |
|---|---|---|---|
| DD | 148 387 | 5/1981 | .......... G01N/27/26 |
| DD | 208 230 | 3/1984 | .......... G01N/27/26 |
| EP | 0 471 986 B1 | 7/1991 | .......... C12M/1/40 |
| WO | WO 97/00441 | 1/1997 | |

* cited by examiner

*Primary Examiner*—Alex Noguerola
(74) *Attorney, Agent, or Firm*—Carol M. LaSalle; Bozicevic, Field & Francis, LLP

(57) ABSTRACT

The present invention provides methods and systems for passively and automatically detecting the presence of a sample (the "sample detection phase") upon application of the sample to a biosensor, identifying the sample detection time and then initiating the measurement of a targeted characteristic, e.g., the concentration of one or more analytes, of the sample (the "measurement phase"), immediately upon sample detection. The subject methods and systems do not employ or involve the application of an electrical signal from an external source to the electrochemical cell for purposes of performing the sample detection phase and are, thus, less complicated and involve fewer steps and components.

17 Claims, 3 Drawing Sheets

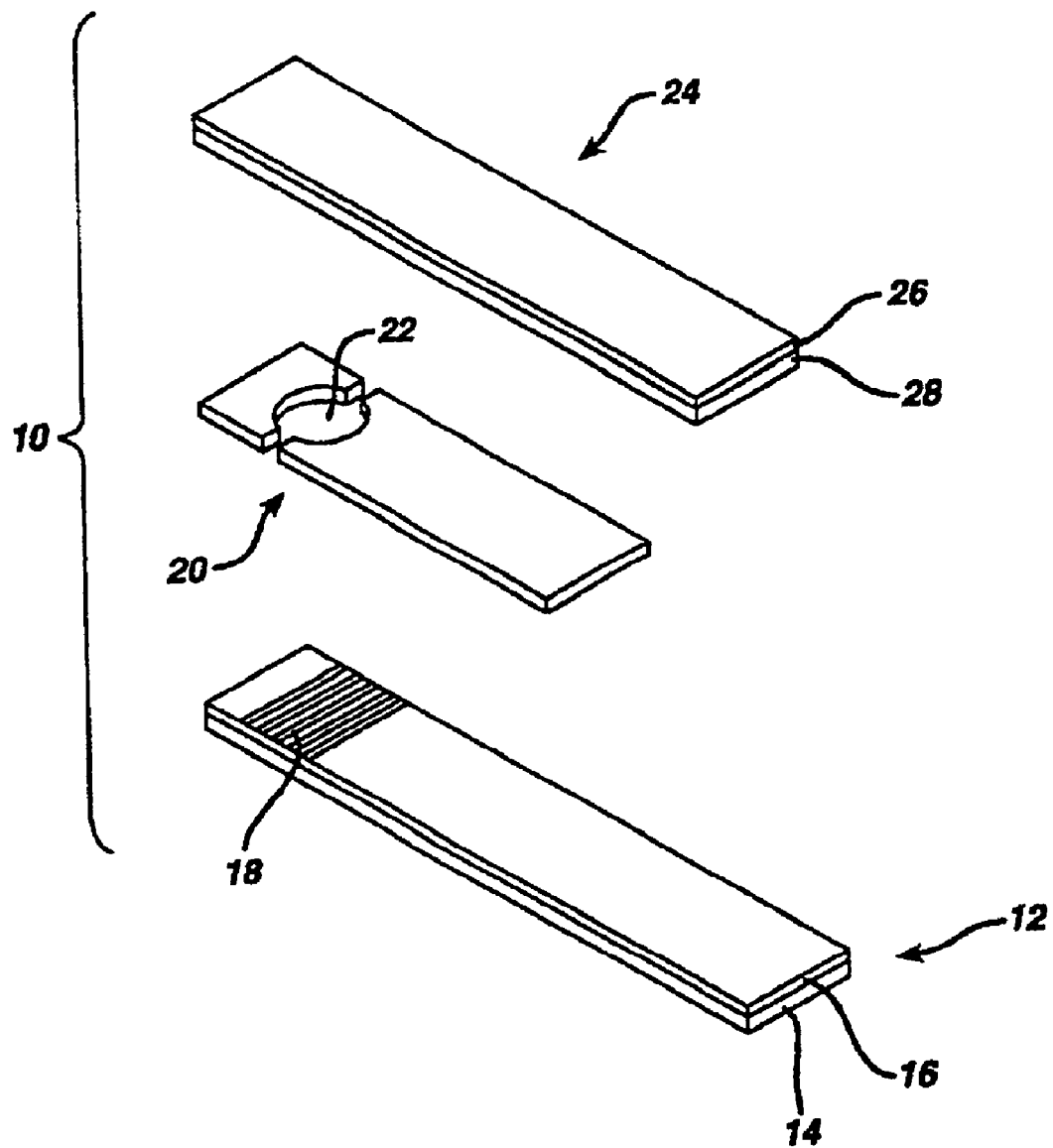
FIG._1

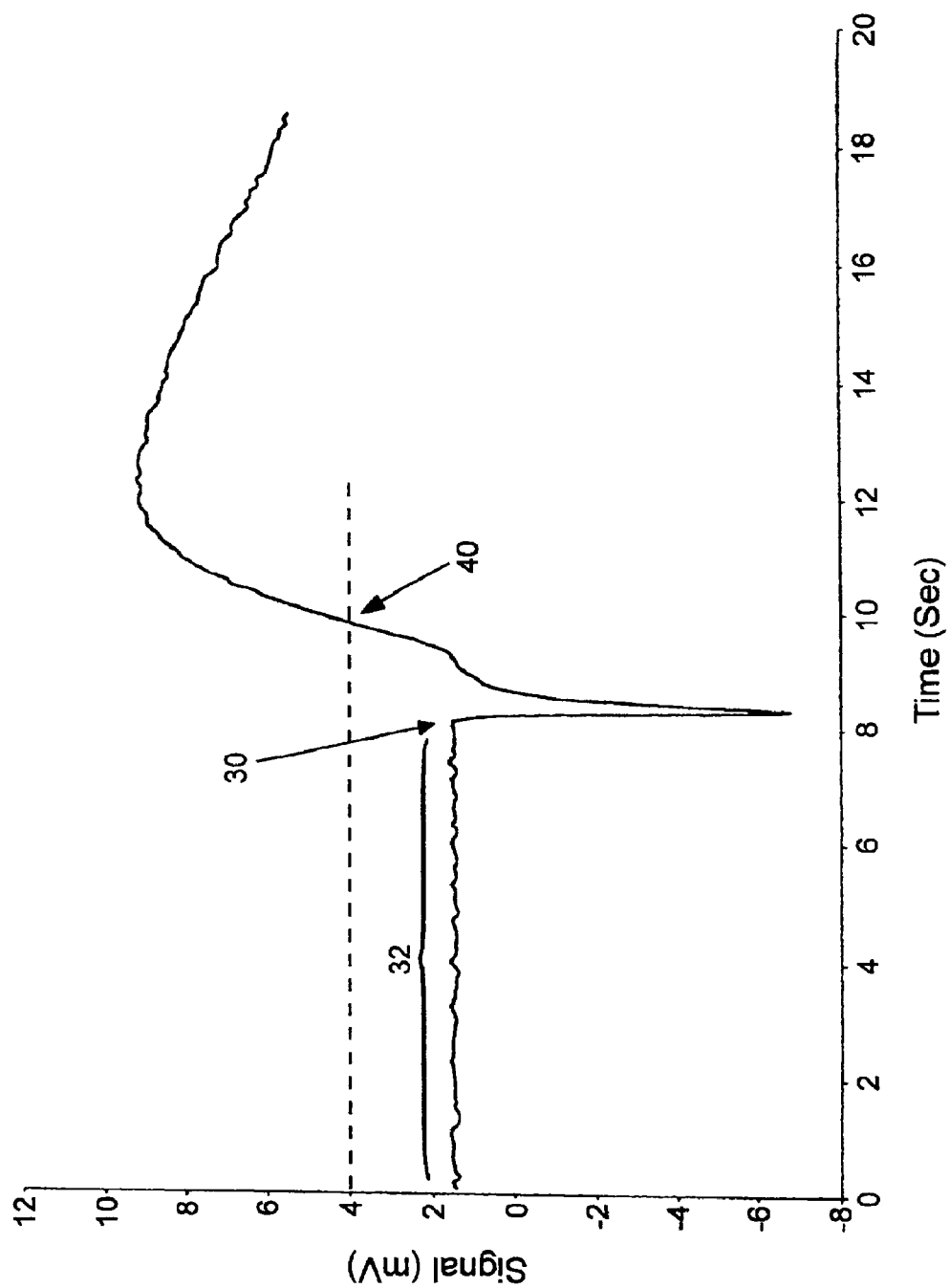
FIG._2

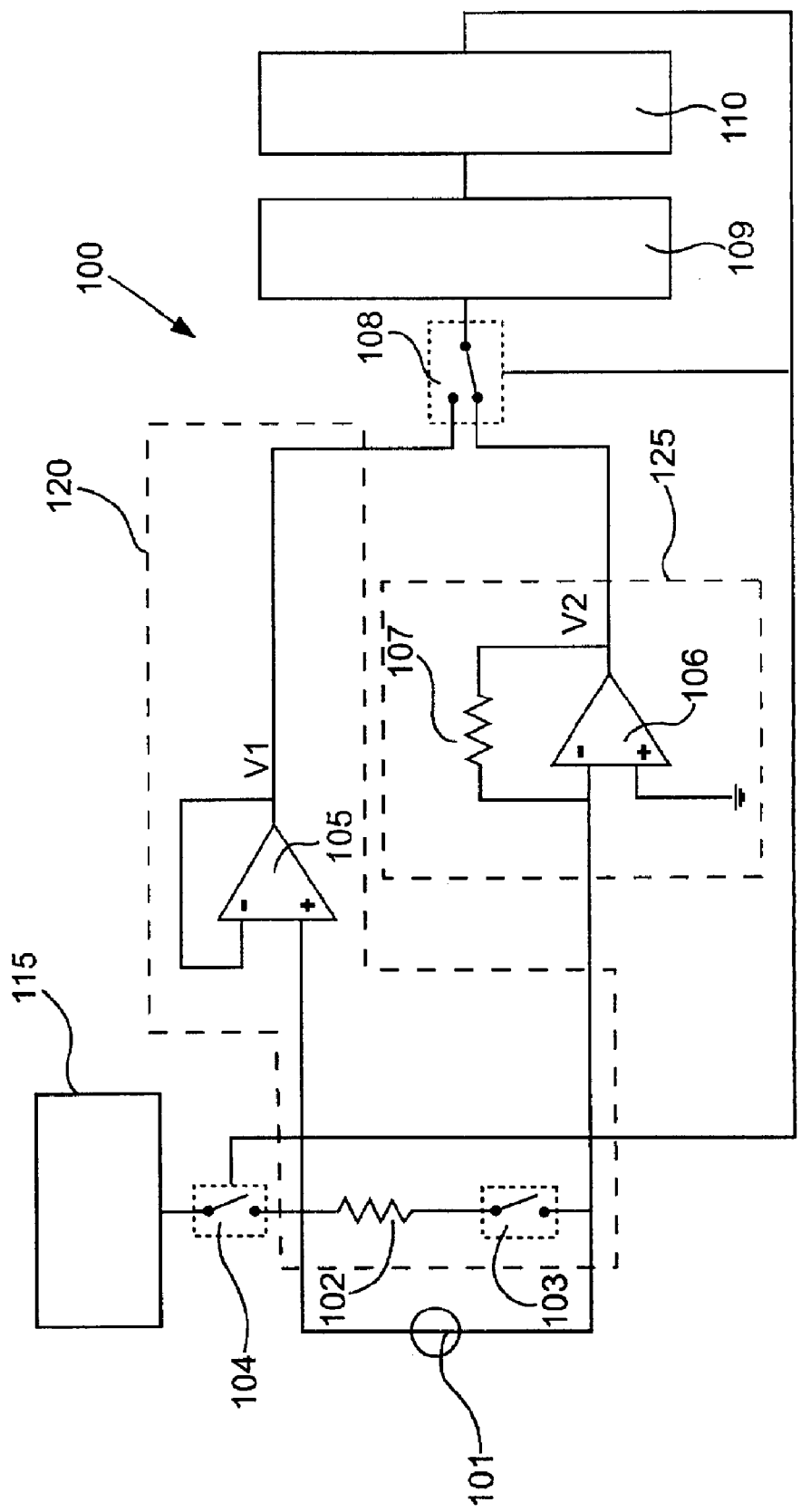
FIG._3

PASSIVE SAMPLE DETECTION TO INITIATE TIMING OF AN ASSAY

FIELD OF THE INVENTION

The present invention relates to the field of electrochemical assays, particularly to the measurement of the concentration of analytes in biological fluid. More particularly, the present invention relates to a system and method for detecting the application of a sample of biological or control fluid to an electrochemical sensor and initiating the timing of the analyte measurement event.

BACKGROUND OF THE INVENTION

Analyte concentration determination in biological fluids, e.g., blood or blood-derived products such as plasma, is of ever increasing importance to today's society. Such assays find use in a variety of applications and settings, including clinical laboratory testing, home testing, etc., where the results of such testing play a prominent role in the diagnosis and management of a variety of disease conditions. Common analytes of interest include glucose for diabetes management, cholesterol for monitoring cardiovascular conditions, and the like. In response to this growing importance of analyte concentration detection, a variety of analyte detection protocols and devices for both clinical and home use have been developed.

One type of method that is employed for analyte detection is an electrochemical-based method. In such methods, a sample of a substance to be tested, e.g., a biological substance typically in aqueous liquid form, e.g., blood, is placed into a reaction zone in an electrochemical cell made up of at least two electrodes, i.e., a counter/reference electrode and a working electrode. Typically, a redox reagent system is present within the reaction zone. Such a reagent system includes at least an enzyme(s) and a mediator. In many embodiments, the enzyme member(s) of the redox reagent system is an enzyme or plurality of enzymes that work in concert to specifically oxidize/reduce the analyte of interest. When the sample is deposited into the electrochemical cell, the targeted analyte comes into contact with the enzyme(s) and reacts therewith forming an oxidisable (or reducible) inactive enzyme. It is a mediator's role to react with an oxidisable (or reducible) enzyme generating a fully active enzyme and a substance, i.e., the product of the reaction between the inactive enzyme and the mediator, in an amount corresponding to the concentration of the targeted analyte. The quantity of the oxidisable (or reducible) substance present is then estimated electrochemically and correlated to the amount of analyte present in the initial biological substance.

The above-described electrochemical cell is commonly used in the form of a disposable test strip on which the biological sample is deposited and which is receivable within a meter by which the electrochemical analyte concentration is determined. Examples of assay systems that employ these types of test strips, often referred to as biosensors, and meters may be found in U.S. Pat. Nos. 5,942,102, 6,174,420 B1 and 6,179,979 B1, the disclosures of which are herein incorporated by reference. These systems can be characterized as coulometric, amperometric or potentiometric, depending on whether the system involves measuring charge, current or potential, respectively, in making the analyte concentration determination.

In electrochemical analyte measurement assays, it is necessary that the measurement system be able to detect the presence of a sample deposited onto a test strip so that the analyte concentration measurement test may be initiated. Moreover, it is important that the presence of sample be detected as soon as the sample comes into contact with the reagent system of the test strip. The timeliness of this detection is important in order to minimize the potential for perturbation of the electrochemical reaction between the target analyte and the reagent system. Perturbation is a change in the equilibrium of the electrochemical cell's reagent system caused by other than the normal and expected reaction progress of the target analyte with the reagent system mediator and enzyme components.

Perturbation is a particularly problematic with amperometric sample detection methodologies, known as "chronoamperometry," which are employed in electrochemical analyte concentration determination methods, and most commonly employed in chronoamperometric assays of an analyte concentration. In many analyte concentration measurement methods, a constant-voltage step function is applied to the test strip, i.e., across the working and reference electrodes, which, upon sample application to the test strip, results in generation of a current through the electrochemical cell of the test strip. The magnitude of the applied voltage must be sufficient to trigger the Faradaic or capacitance current flow in the cell to provide rapid sample detection. When the current produced as a result of this applied voltage exceeds a predetermined threshold value, the system, i.e., the meter, "stamps" this time as the beginning of the analyte concentration measurement phase, and thus, initiates measurement of the current at the working electrode to determine the concentration of the targeted analyte. The electrochemical reaction between the redox reagent system and the biological sample is initiated prior to the system being ready to accurately stamp or mark the actual time of initiation of the analyte concentration measurement phase. As such, a fraction of the current produced as a result of this electrochemical reaction is used as part of the sample detection phase. Thus, the finally measured current is not an accurate representation of the analyte concentration of the sample. In other words, during the time prior to achieving the predetermined current value, i.e., prior to the sample detection time, the voltage applied to the cell will "perturb" the electrochemical reaction between the target analyte and the reagents. The shorter the device response time and/or the higher the applied voltage prior to achieving the requisite current threshold value, the greater the perturbation of an electrochemical reaction and, thus, the less accurate the analyte concentration measurement is likely to be.

Another disadvantage of the chronoamperometric method is that it is more likely to produce an inaccurate measurement with samples containing low concentrations of the targeted analyte or high concentrations of red blood cells or both. As the current produced upon application of voltage to the electrochemical cell generally decreases with decreasing analyte concentration (or with an increase in hematocrit levels), the longer the sample detection time the less likely the measured current will be an accurate representation of analyte concentration. On the other hand, setting a lower current threshold level will likely make the system more sensitive and falsely trigger by noise.

Another known sample detection method is disclosed in U.S. Pat. No. 6,193,873 B1, which is hereby incorporated by reference. This patent discloses a chronopotentiometric method which overcomes the problem of perturbation associated with chronoamperometric methods of sample detection. Instead of applying a constant-voltage step function, the chronopotentiometric method involves applying a small, constant-current step function to the test strip. The voltage across the working and reference electrodes is then monitored. Only when this voltage falls below a certain threshold voltage is the measurement of the analyte made by switching from application of a constant current to a constant voltage mode. Because a larger proportion of the resulting current measured following this point is representative of the analyte concentration, this method is far more accurate than the chronoamperometric method of sample detection determination.

In order to practice the method of the '873 patent, it is necessary to employ electronic circuitry which provides both a current source for the supply of the constant-current step function to the reagent test strip for performing the sample detection phase, as well as a voltage source for performing the analyte concentration measurement phase of the method. As such, the electronic circuitry further includes the necessary components to allow switching from the application of the current supply to application of the voltage supply at the precise time that the sample detection phase is complete.

Thus, it would be beneficial to provide an improved method of very accurately, expeditiously and immediately detecting the presence of a sample applied to an electrochemical test strip. Of particular benefit would be such a method and a system for implementing such method which do not require the application of a constant current or voltage step function for purposes of detecting the presence of a sample on a test strip. Preferably, such a system would require fewer electronic components than the one described in '873 patent.

SUMMARY OF THE INVENTION

The present invention provides methods and systems for passively and automatically detecting the presence of a sample applied to a biosensor (the "sample detection phase") upon application of the sample, and then initiating the measurement of a targeted characteristic, e.g., the concentration of one or more analytes, of the sample (the "measurement phase"), immediately upon sample detection.

As discussed above, prior art methods of sample detection involve application of an electrical input signal, either a voltage step function (as with chronoamperometry) or a current step function (as with chronopotentiometry), prior to placement of the biological sample within the electrochemical cell. With either approach, the measurement phase is not commenced until a threshold level is achieved by the electrical signal produced, a current signal or a voltage signal, respectively, as a result of the application of the electrical input signal.

The inventors have discovered that the presence of a sample can be detected, and the measurement phase appropriately and timely commenced, without applying a sample detection phase electrical signal to the electrochemical cell. As such, the subject methods do not employ or involve the application of an electrical signal from an external source to the electrochemical cell for purposes of performing the sample detection phase. With the present invention, this phase is commenced passively, solely by placement of a sample within the electrochemical cell, thereby bridging the gap between the electrodes and generating a signal, i.e., a voltage signal. Alternatively one can place a resistor across the electrodes and obtain a current signal, indicative of the sample presence within the cell. Upon detection of the presence of the sample, the sample detection time is noted or recorded, and a measurement related electrical signal, i.e., a voltage signal, is automatically applied across the electrochemical cell for purposes of testing the sample for a selected characteristic. After a predetermined period of time has lapsed since sample detection, the resulting current response is measured. From this measured current, or its integration over time, the analyte concentration is then calculated.

The subject methods provide significant advantages over prior art methods for sample detection. Because there is no external electrical signal applied to the sample prior to the measurement phase, the sample detection phase of the subject methods does not create any perturbation of the sample. Thus, the value of the resulting output signal from the measurement phase represents only the amount (e.g., volume, percentage, etc.) of the characteristic of the sample being measured, a far more accurate measurement than what is provided by many prior art methods.

Another advantage of the present invention is the elimination of false or inaccurate analyte measurements due to damaged or mishandled electrodes. With the prior art analyte measurement systems mentioned above, any damage (e.g., a short circuit) to either the test strip electrodes or the meter contacts may automatically initiate the analyte measurement assay, even without sample being present within the cell. Because the present invention does not involve the application of an external electrical signal for purposes of sample detection, an assay can only be initiated upon deposit of the sample solution within the electrochemical cell of the biosensor.

Because the subject methods are simpler than prior art methods, involving fewer steps, the system and components necessary to perform the subject methods is less complex than for prior art methods of sample detection. More particularly, because the subject methods do not require application of an external voltage or current for purposes of the sample detection phase, the subject systems do not require inclusion of such designated energy sources and, thus, are less complicated and involve fewer components than prior art systems. The systems of the present invention include electronic circuitry and components that may be incorporated or provided integrally with a meter for receiving a biosensor, such as an electrochemical test strip to which the sample volume of biological solution is deposited, for purposes of measuring a selected characteristic, e.g., the concentration of selected analytes of interest, of the sample. The electrochemical test strip, as will be more fully described below, includes an electrochemical cell comprised of at least two electrodes, i.e., a working and a reference/counter electrode, between which a reaction zone is defined for receiving the biological sample.

Also provided by the present invention are kits which include test strip meters which incorporate the subject systems for practicing the subject methods.

While the subject methods, systems and kits may be used to detect different types of biological samples, such as blood, urine, tears, saliva, and the like, applied to various types of electrochemical cells for the measurement of various characteristics, such as analyte concentrations, they are particularly well suited for the detection of samples of blood or blood fractions and the like as applied to the electrochemical cell of a test strip for the determination of glucose concentration therein.

These and other objects, advantages, and features of the present invention will become apparent to those persons skilled in the art upon reading the details of the methods and systems of the present invention which are more fully described below.

BRIEF DESCRIPTION OF THE DRAWINGS

FIG. 1 is an exploded view of an electrochemical test strip for use with the present invention.

FIG. 2 is a graph of the voltage profile across an electrochemical test strip vs. time for the method of the present invention.

FIG. 3 is a schematic diagram of an electronic circuit of a system of the present invention operatively coupled to an electrochemical biosensor for practicing the subject method.

DETAILED DESCRIPTION OF THE PREFERRED EMBODIMENTS

The present invention provides methods and systems for automatically detecting the presence of a sample applied to a biosensor (the "sample detection phase") and then initiating the measurement of a targeted characteristic, e.g., the concentration of one or more analytes, of the sample (the "measurement phase") immediately upon sample detection. The sample detection phase of the subject methods is performed passively, immediately upon application of a sample to a biosensor, without application of a voltage step function (as with chronoamperometry) or current step function (as with chronopotentiometry). The subject systems include electronic circuitry for performing these steps. Also provided by the present invention are kits that include a test strip meter which incorporate the subject systems for practicing the subject methods.

Before the present invention is described in further detail, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publications provided may differ from their actual publication dates, which may need to be independently confirmed.

The present invention will now be described in detail. An exemplary electrochemical biosensor usable with the systems and employable by the methods of the present invention will be described first. Next, an explanation is provided of the premise of the present invention and of the particular discoveries made by the inventors, followed by a detailed description of the subject methods and the subject systems, as well as a description of the subject kits. In the following description, the present invention will be described in the context of analyte concentration measurement applications; however, such is not intended to be limiting and those skilled in the art will appreciate that the subject systems and methods are useful in measurement of other physical and chemical characteristics of biological substances.

Electrochemical Biosensors

The subject methods and systems are usable with a biosensor, more particularly an electrochemical cell-based biosensor, into which the sampled biological material is deposited or transferred. There are varying designs of electrochemical cell-based biosensors. The most common of these designs employed in the field of analyte concentration monitoring include test strip configurations, such as those disclosed in U.S. Pat. No. 6,193,873 and in copending U.S. patent application Ser. Nos. 09/497,304; 09/497,269; 09/736,788 and 09/746,116, the disclosures of which are herein incorporated by reference. Such test strips are used with meters configured for electrochemical measurements, such as those disclosed in the above-identified patent references.

Electrochemical biosensors other than test strips may also be suitable for use with the present invention. For example, the electrochemical cell may have a cylindrical configuration wherein a core electrode is co-axially positioned within a second tubular electrode. Such electrochemical cell configurations may be in the form of micro-needles and, as such, are either integral within the needle structure for in situ (e.g., typically under the skin surface) measurements or otherwise in physical or fluid communication with a micro-needle structure. Examples of such micro-needle are disclosed in copending U.S. patent application Ser. Nos. 09/878,742 and 09/879,106 filed on Jun. 12, 2001, hereby incorporated by reference. For purposes of this disclosure, the subject devices will be described in use with electrochemical cells in test strip configurations; however, those skilled in the art will appreciate that the subject devices may be used with any suitable electrochemical cell configuration, including micro-needle configurations.

The type of electrochemical measurement that is made may vary depending on the particular nature of the assay and the meter with which the electrochemical test strip is employed, e.g., depending on whether the assay is coulometric, amperometric or potentiometric. The electrochemical cell will measure charge in a coulometric assay, current in an amperometric assay and potential in a potentiometric assay. For purposes of this disclosure, the present invention will be described in the context of amperometric assays; however, the subject devices may be employed with any type of assay and electrochemical measurement.

Generally, in any configuration, an electrochemical cell includes at least two electrodes, a working and a reference/ counter electrode, spaced-apart in either a facing arrangement or in a side-by-side arrangement in the same plane. In the first arrangement, the electrodes are separated by a thin spacer layer, which defines a reaction area or zone, or chamber into which a biological sample is deposited or transferred for analyte concentration measurement. In the side-by-side configuration, the electrodes are in a chamber with a defined thickness and volume. Present in the reaction area or chamber, i.e., coated on one or more of the facing surfaces of the electrodes, are one or more redox reagents selected to chemically react the target analyte(s). Such redox reagents typically comprise at least one enzyme and a mediator. It should also be noted that electrochemical cells can have two or more electrodes, i.e., one working electrode and one counter/reference electrode, one working electrode and one counter electrode and one reference electrode, two working electrodes and one counter/reference electrode, etc. Depending on the type of application, it may be more desirable to have more than two electrodes in the electrochemical cell to allow for a more accurate voltage application or perhaps for measuring more than one analyte.

A representation of an exemplary electrochemical test strip 10 suitable for use with the present invention is provided in the exploded view of FIG. 1. Test strip 10 is made up of a bottom layer 12 and a top layer 24 separated by a thin spacer layer 20 which has a cutaway section that defines a reaction zone or area 22. Generally, bottom and top layers 12 and 24 are configured in the form of elongated rectangular strips each having a length in the range from about 2 to 6 cm, usually from about 3 to 4 cm, having a width in the range from about 0.3 to 1.0 cm, usually from about 0.5 to 0.7 cm, and having a thickness in the range from about 0.2 to 1.2 mm, and usually from 0.38 to 0.64 mm.

Bottom layers 12 and 24 each define a substrate base, 14 and 26, respectively, made of an inert support or backing material on which has been deposited, typically by sputtering, a conductive material which form the reference and working electrodes, 16 and 28, respectively. The inert backing material is typically rigid material and capable of providing structural support to each of the electrodes 16 and 28 and, in turn, the electrochemical test strip as a whole. Such suitable materials include plastics (e.g., PET, PETG, polyimide, polycarbonate, polystyrene, polyester), silicon, ceramic, glass, and the like. The conductive material is preferably a metal, where metals of interest include palladium, gold, platinum, iridium, doped indium tin oxide, stainless steel, carbon and the like. For example, a palladium coating may form working electrode 16 while a gold coating forms reference electrode 28.

Spacer layer 20 is positioned or sandwiched between electrodes 16 and 28. The thickness of spacer layer 12 generally ranges from about 1 to 500 $\mu$m, and usually from about 50 to 150 $\mu$m. Spacer layer 20 may be fabricated from any convenient material, where representative suitable materials include PET, PETG, polyimide, polycarbonate and the like. The surfaces of spacer layer 20 may be treated so as to be adhesive with respective electrodes 16 and 28 and thereby maintain the structure of the electrochemical test strip 10.

Spacer layer 20 is cut so as to provide a reaction zone or area 22 having any appropriate shape including circular, square, triangular, rectangular, or irregular shaped reaction areas. The top and bottom of the reaction zone 22 is defined by the facing surfaces of electrodes 16, 28 while spacer layer 20 defines the sidewalls of the reaction area 22. The volume of the reaction area ranges from at least about 0.1 to 10 $\mu$l, usually from about 0.2 to 5.0 $\mu$L and more usually from about 0.05 to 1.6 $\mu$L.

Present in the reaction area 22, deposited near one end 18 of electrode 16, is a redox reagent system, generally referred to as a signal producing system, which provides for the specific reagent components that chemically interact with the target analyte to derive the concentration of analyte in the biological sample. The redox reagent system or signal producing system typically includes at least one enzyme component and a mediator component. In many embodiments, the enzyme component includes one or more enzymes that work in concert to oxidize/reduce the analyte of interest. In other words, the enzyme component of the redox reagent system is made up of a single analyte oxidizing/reducing enzyme or a collection of two or more enzymes that work in concert to oxidize/reduce the analyte of interest. Typical enzymes of interest include oxidoreductases, hydrolases, transferases, dehydrogenases, esterases, and the like; however, the specific enzyme present in the reaction area depends on the particular analyte for which the electrochemical test strip is designed to detect. Where the analyte of interest is glucose, for example, suitable enzymes include glucose oxidase, glucose dehydrogenase (either $\beta$-nicotinamide adenine dinucleotide based (NAD) or 4,5-Dihydro-4,5-dioxo-1H-pyrrolo[2,3-f] quinoline-2,7,9-tricarboxylic acid based (PQQ)). Where the analyte is cholesterol, suitable enzymes include cholesterol esterase and cholesterol oxidase. For other analytes, enzymes including but not limited to lipoprotein lipase, glycerol kinase, glycerol-3-phosphate oxidase, lactate oxidase, lactate dehydrogenase, pyruvate oxidase, alcohol oxidase, bilirubin oxidase, uricase, sarcosine oxidase, ascorbate oxidase, glutamate oxidase, peroxidases, and the like may be used.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, phenothiazine derivatives, phenoxazine derivatives, metalloporphyrin derivatives, phthalocyanine derivatives, viologen derivatives, ferrocene derivatives, osmium bipyridyl complexes, ruthenium complexes and the like. In those embodiments where glucose is the analyte of interest and glucose oxidase or glucose dehydrogenase is the enzyme component, a mediator of particular interest is ferricyanide, discussed in more detail below in the context of the description of the subject methods. Other reagents that may be present in the reaction area include buffering agents, e.g., citraconate, citrate, phosphate, "Good" buffers and the like.

The redox reagent system is generally present in dry form. The amounts of the various components may vary, where the amount of enzyme component typically ranges from about 0.1 to 20% by weight.

Premise of the Invention

As mentioned above, the inventors have discovered that the presence of a sample within an electrochemical cell can be detected, and the measurement phase appropriately and timely commenced, without applying a sample detection phase electrical signal to the electrochemical cell. This discovery is based on the determination by the inventors that certain chemical substances, when used as mediator components of the redox reagent system employed in the electrochemical cell and caused to electrochemically react with the applied sample, produce a potential difference across the electrodes of the electrochemical cell in the absence of or without the application of an electrical signal to the cell from an external energy source.

Such a potential difference is produced as a result of the asymmetric deposition of the redox reagent system, and more particularly the oxidizable mediator component (e.g., ferricyanide in glucose concentration determinations) of the redox reagent system, at the electrodes or, more commonly, the deposition of the reagent system on only one of the electrodes. In either case, the concentration of the reagent system or the oxidizable mediator component is greater at one electrode, e.g., the working electrode, than at the other electrode, e.g., the reference/counter electrode. The chemical reaction between the reagent system and the sample solution produces a reduced mediator (e.g., ferrocyanide when ferricyanide is the oxidized mediator) in an amount, which is a relatively small fraction at the short time scale. It is the asymmetric concentration of the redox reagent system between the electrodes that generates a potential difference across the electrodes. The value of this generated potential difference is proportional to the ratio of the concentration of the oxidized mediator to the concentration of reduced mediator, e.g., the ferricyanide-to-ferrocyanide concentration ratio. This relationship is represented by the following equation, known as the Nernst Equation:

$$E = \frac{RT}{nF} \ln \frac{[O]_1 [R]_2}{[O]_2 [R]_1}$$

wherein E is the potential difference generated across the electrodes; R is the universal gas constant (8.31441 VCmol$^{-1}$K$^{-1}$); T is the temperature within the electrochemical cell; n is the number of electrons involved in the redox reaction; F is Faraday's constant (96,485 C/mole); $[O]_1$ and $[O]_2$ are the concentrations of the oxidized mediator at the working and reference/counter electrodes, respectively; and $[R]_1$ and $[R]_2$ are the concentrations of the reduced mediator at the working and reference/counter electrodes, respectively. By configuring a system wherein the sample detection threshold voltage is set to the expected value of the generated potential difference, the measurement phase of the subject methods can be initiated upon the immediate detection of such threshold voltage. This threshold voltage is typically in the range from about 3 to 6 mV. It should also be noted that more than one redox couple may be used for helping generate a larger voltage. In this scenario, both redox couples must be discretely deposited on their own respective electrode. Alternatively, the electrode material itself may behave as the redox couple if materials such as Ag, Ag/AgCl, Zn, Ni, or Cu are used.

The present invention may be used in many applications, e.g., in the concentration measurements of many types of analytes, using a variety of mediators. Suitable mediators for use with the present invention in measuring glucose concentrations within a sample include but are not limited to ferricyanide, ferrocene, ruthenium and osmium complexes.

Methods of the Invention

Accordingly, based on the above premises, the inventors have determined that the presence of a sample in an electrochemical cell can be detected, and the measurement phase appropriately and timely commenced, without applying a sample detection phase electrical signal to the electrochemical cell. As such, the subject methods do not employ or involve the application of an electrical signal to the electrochemical cell for purposes of performing the sample detection phase. With the present invention, this phase is commenced passively, solely by placement of a sample within the electrochemical cell.

The steps of the subject methods are now described, with reference to FIG. 2, in the context of an analyte concentration measurement performed on a biological sample using an electrochemical test strip operatively placed in a meter of the type mentioned above. In practicing the subject methods, the test strips used for the analyte concentration measurement are provided having a redox reagent system provided within its electrochemical cell wherein the reagent system comprises a mediator component, e.g., ferricyanide, having chemical characteristics such that a potential difference occurs within the electrochemical cell upon the electrochemical reaction with a sample, as explained in detail above.

In practicing the subject methods, a biological sample, e.g., a blood sample or a control solution (for purposes of verifying or trouble shooting the test system integrity), is obtained and placed, deposited or transferred to within the test strip cell in the absence of an externally applied electrical signal. Placement of the sample within the test strip may be accomplished by first inserting the test strip into the test meter and then applying the sample to the test strip ("on-meter dosing").

It is the application of the sample, designated by arrow 30 of FIG. 2, to the electrochemical cell of the test strip by which the sample detection phase of the subject methods is initiated. The sample acts to bridge the gap between the working and reference/counter electrodes. Since this gap is initially dry, only negligible current flows between the electrodes prior to application of the wet sample. The resulting voltage produced by this negligible, pre-sample-application current flow is due to the offset of operational amplifier 106, and is typically in the range from about −2 mV to +2 mV, as indicated by bracket 32 of FIG. 2. Thus, the wet sample forms a conductive path between the electrodes thereby causing a potential difference across the electrodes. The potential difference or voltage across the electrodes is monitored, and when the monitored voltage is detected to have increased above a predefined threshold voltage, designated as the sample detection time (indicated by arrow 40 in FIG. 2), the analyte concentration measurement is then immediately commenced. Typically, such predefined threshold voltage is in the range from about 3 to 6 mV. As such, the subject methods provide a means of very accurately determine the point in time at which the sample to be tested contacts the test strip so that the duration of the measurement event may be accurately timed. The first derivative of the voltage signal is also an indication of how fast the voltage is generated when sample is applied to the cell and can be used for sample application detection.

Commencement of the measurement phase, designated by arrow 40 of FIG. 2, involves application of a predetermined test voltage level by a voltage source external to the test strip. Generally, such test voltage ranges from about 0 to 600 mV. The resulting current, produced from the electrochemical cell is then measured as a function time. After a predetermined time, the value of the measured current is determined to be representative of the concentration of the target analyte. Such predetermined time is generally in the range from about 3 to 40 seconds, and more typically in the range from about 4 to 20 seconds. Alternatively, the representative current value may be an average of a plurality of measurements of the resulting current taken at predetermined time intervals during the predetermined time. Still yet, the continuous measured current could be integrated over a predetermined period of time. With any of these current measurement protocols, the duration of this predetermined time is generally at least about 3 seconds when the sample is blood and the target analyte is glucose. That duration generally provides sufficient time for the reagents to dissolve and for the mediator to be reduced in an amount that is readily measurable. The concentration of the analyte is then derived or calculated using the measured current value (whether a single, discrete measurement, an average a plurality of measurements or a continuous integrated measurement).

Systems for Practicing the Invention

As mentioned above, the present invention also includes systems for carrying out the subject methods. The subject systems include electronic components and/or circuitry intended to be used with and electronically coupled to a biosensor, such as a disposable test strip previously described, into which the sampled solution to be tested is placed. Most typically, such electronic circuitry is incorporated into a meter or other automated device configured to receive and operatively engage with such test strip and to measure one or more physical or chemical characteristics, e.g., analyte concentration, of a biological sample held within the electrochemical cell. Such electronic circuitry may comprise discrete electronic components and/or integrated circuits having multiple circuit elements, e.g., an ASIC (Application Specific Integrated Circuit) and/or semiconductor devices, e.g., a microprocessor suitably programmed to execute certain steps or functions of the subject methods based on certain signal or data inputs received from the electrochemical cell and to store and record data, both static and dynamic. In certain embodiments, the systems of the present invention include such electronic circuitry and such an automated measurement device or meter, wherein the electronic circuitry is completely structurally and functionally integral with the automated measurement device.

FIG. 3 is a schematic diagram of an embodiment of a system or electronic circuit 100 of the present invention suitable for practicing the methods of the present invention. Such embodiment is intended to be exemplary and not limiting to the manner in which the subject methods can be implemented. Circuit 100 is configured to be electrically connectable to a test strip 101, and generally includes a voltage source 115, a sample detection sub-circuit 120, an analyte concentration measurement sub-circuit, more specifically a current to voltage converter 125, switches 104 and 108, an analog-to-digital converter 109 and a microprocessor 110. Those skilled in the art will recognize other circuit arrangements and components that are suitable for carrying out the steps of the subject methods.

In performing the subject methods, circuit 100 is electronically coupled to a test strip 101. Initially, switch 103 of sample detection sub-circuit 120 is in a closed position, switch 104 is an open position and switch 108 is in the "up" position. As such, sample detection sub-circuit 120 is operatively electrically engaged with test strip 101, and resistor 102 of sub-circuit 120 is placed across the electrodes of test strip 101. Resistor 102 prevents false triggering due to environmental noise prior to application of a sample to test strip 101. Sample detection sub-circuit 120, comprised of operational amplifier 105, monitors the transient voltage ($V_1$) across the strip electrodes. Transient voltage $V_1$, via switch 108, is provided to A/D converter 109 where it is converted to a digital signal which is then transmitted to microprocessor 110. Microprocessor 110 continuously compares the digital value of $V_1$ to a predetermined voltage stored in its memory. Such predetermined voltage is representative of the sample detection threshold voltage proportional to the concentration of the mediator redox couple components, ie., the oxidized/reduced mediator concentration ratio, e.g., ferricyanide/ferrocyanide concentration ratio, discussed above.

At the point in time at which microprocessor 110 detects that the generated potential difference or voltage $V_1$ has reached the sample detection threshold voltage, microprocessor 110 records such time, designated as the sample detection time which defines t=0 for the analyte concentration measurement phase. At the sample detection time, microprocessor 110 also transmits control signals to open switch 103, close switch 104 and move switch 108 to the "down" position, respectively. As such, resistor 102 and sub-circuit 120 are disconnected from test strip 101, and voltage source 115 is operatively connected to test strip 101, thereby applying the desired or predetermined test voltage across the electrodes of test strip 101. The electrical signal, e.g., current signal, generated by the test strip cell is detected by measurement sub-circuit 125, comprised of operational amplifier 106 and resistor 107, which acts to convert the detected current to a voltage signal ($V_2$) representative of the concentration of the targeted analyte within the sample. Via switch 108, this voltage signal $V_2$ is converted to a digital signal by A/D converter 109. This digital value is then received by microprocessor 110 which then derives or calculates the concentration of the target analyte from the measured current signal. This analyte concentration value may then be transmitted to a display unit (not shown).

In addition to the advantages previously mentioned, the present invention has inherent safeguards against unintentionally triggering the system circuit and initiating the analyte measurement phase, thereby avoiding false measurements of the analyte. Since the resistivity of the sample is not a criterion for detecting application of the sample, passive loads, cannot accidentally trigger the circuit to perform the measurement phase of the subject methods. Additionally, if the chemistry of the test strip has been damaged or is not suitable, e.g., the oxidizable mediator component is missing from the redox reagent system, application of the sample solution to the test strip does not create the requisite chemical reaction and, thus, a voltage cannot develop across the cell electrodes, and thus, the circuit cannot be triggered. Also, once the electrochemical has been filled with a sample and reached equilibrium, i.e., the concentration of the oxidized mediator at both electrodes is the same, no potential difference can be generated across the cell, thus, eliminating the risk of re-triggering the circuit. Still yet, the system will not perform a measurement test if the sample solution does not contain the analyte for which the redox reagent system was designed. This is due to the fact that the present invention utilizes a mediator in the oxidized state which is converted to the reduced state only in presence of analyte and enzyme. The presence of the asymmetric distribution of two redox mediator states drives the generation of a measured voltage.

Kits

Also provided by the subject invention are kits for use in practicing the subject methods. The kits of the subject invention include a subject system including the electronic circuitry, as described above, or in the form of a meter or other automated instrument, as described above, for passively detecting the application of a biological sample to an electrochemical cell to accurately initiate the analyte concentration measurement process.

The kits may further include instructions for using the subject systems according to the subject methods with such electrochemical cell in the form of a test strip or microneedle or the like in the detection of the applied sample or material held within the electrochemical cell. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description that the features of the subject methods and systems overcome many of the disadvantages of prior art techniques for sample detection in the context of electrochemical analyte concentration analysis, and provide certain advantages including, but not limited to, eliminating the risk of perturbation of the sample, simplifying the components necessary to carry out the sample detection, safeguarding against unintentional triggering of the testing process, and providing a very accurate way for initiating the timing of the analyte concentration measurement process. Further, such sample volume determination is not subject to variations of blood glucose concentration, blood hematocrit level, the blood donor, testing temperature, and the concentration of interferences often present in blood samples. As such, the subject invention represents a significant contribution to the field of biological sample application detection and analyte concentration measurement.

The subject invention is shown and described herein in what is considered to be the most practical and preferred embodiments. It is recognized, however, that departures may be made there from, which are within the scope of the invention, and that obvious modifications will occur to one skilled in the art upon reading this disclosure.

The specific methods and systems disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A method for measuring the concentration of an analyte of a sample that is applied to an electrochemical cell, comprising the steps of:
    applying said sample to said electrochemical cell in the absence of an external electrical signal applied to said electrochemical cell;
    monitoring the potential difference across the electrochemical cell;
    determining a sample detection time by noting when said potential difference increases above a predetermined threshold voltage;
    applying a predetermined test voltage to said electrochemical cell;
    measuring an electrical response to said applied predetermined test voltage at a predetermined time after applying said predetermined test voltage; and
    calculating said analyte concentration using said measured electrical response.

2. The method of claim 1 wherein said electrochemical cell comprises a chemical component for reacting with said sample and wherein said predetermined test voltage is determined based on said chemical component.

3. The method of claim 2 wherein said chemical component is ferricyanide.

4. The method of claim 3 wherein said predetermined test voltage is in the range from about 0 to 600 mV.

5. The method of claim 1 wherein said electrical response is the current through said electrochemical cell.

6. The method of claim 1 wherein said predetermined time is in the range from about 3 to 40 seconds.

7. The method of claim 1 wherein said electrical cell comprises two spaced-apart electrodes and a reagent system within the area between said electrodes, and wherein said potential difference is produced by the reaction of said reagent system with said sample.

8. The method of claim 7 wherein said reagent system comprises an enzyme component and a mediator component, wherein said enzyme component is selected for reacting with said analyte and wherein said mediator component determines said predetermined test voltage.

9. A method for measuring the concentration of an analyte of a sample, comprising the steps of:
    providing an electrochemical cell comprising a signal producing system comprising an enzyme component selected for reacting with said analyte and a reducible/oxidizable mediator component selected for reacting with said enzyme component;
    monitoring the potential difference across the electrochemical cell;
    applying said sample to said electrochemical cell wherein said analyte causes said enzyme component and said reducible/oxidizable mediator component to dissolve and thereby release a oxidized/reduced mediator component;
    determining a sample detection time by noting when said potential difference falls below a predetermined threshold voltage;
    applying a predetermined test voltage to said electrochemical cell;
    measuring the current in response to said applied predetermined test voltage at a predetermined time after applying said predetermined test voltage; and
    calculating said analyte concentration using said measured current.

10. The method of claim 9 wherein said analyte is glucose, said mediator component is ferricyanide and said substance is ferrocyanide.

11. The method of claim 9 wherein said potential difference is proportional to the concentration of said reducible/oxidizable mediator component to said oxidized/reduced mediator component.

12. A system for measuring analyte concentration in a sample that has been applied between a working and reference/counter electrode of an electrochemical cell, comprising, in electrical communication:
    means for isolating said electrodes from application of an electrical signal from a source external to said electrochemical cell;
    means for monitoring a potential difference across the electrodes;
    means for determining when said potential difference falls below a predetermined threshold voltage to indicate sample detection;
    means responsive to sample detection for applying a predetermined test voltage to said sample;
    means for measuring a resulting electrical response to said applied predetermined test voltage; and
    means for calculating said analyte concentration by using said measured electrical response.

13. The system of claim 12 wherein said system is a meter configured for operatively receiving said electrochemical cell.

14. The system of claim 12 wherein said electrochemical cell is configured within a test strip.

15. The system of claim 12 wherein said electrochemical cell is configured within a microneedle.

16. A kit for measuring analyte concentration in a biological sample to be applied to an electrochemical test strip, comprising:
   a system according to claim 12 configured to received said test strip and to measure said analyte concentration; and
   instructions for using said system to measure analyte concentration in said biological sample.

17. The kit of claim 16 further comprising at least one electrochemical test strip comprising an electrochemical cell comprising a signal producing system comprising an enzyme component selected for reacting with said analyte and a mediator component selected for oxidizing said enzyme component to an active form, where said mediator component contains a substance which upon dissolution of reagent within said cell causes a potential difference to be generated across the electrochemical cell.

* * * * *